(12) United States Patent
Yang

(10) Patent No.: US 9,182,346 B2
(45) Date of Patent: Nov. 10, 2015

(54) TRANSMITTANCE TESTING APPARATUS

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventor: Shengji Yang, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 14/236,216

(22) PCT Filed: Apr. 8, 2013

(86) PCT No.: PCT/CN2013/073901
§ 371 (c)(1),
(2) Date: Jan. 30, 2014

(87) PCT Pub. No.: WO2014/131224
PCT Pub. Date: Sep. 4, 2014

(65) Prior Publication Data
US 2015/0042997 A1    Feb. 12, 2015

(30) Foreign Application Priority Data
Feb. 26, 2013 (CN) .......................... 2013 1 0060534

(51) Int. Cl.
   *G01N 21/55* (2014.01)
   *G01N 21/59* (2006.01)
   *G01N 21/01* (2006.01)
(52) U.S. Cl.
   CPC ............... *G01N 21/59* (2013.01); *G01N 21/01* (2013.01)

(58) Field of Classification Search
   CPC .......... G01N 2021/9513; G01N 21/95; G01N 15/1468; G01N 2015/1472; G01N 2021/4719; G01N 21/956; G01N 21/958; G01B 11/0675; G01B 2290/45; G01B 2290/70; G01B 9/02007; G01B 9/02027; G01B 9/02043
   See application file for complete search history.

(56) References Cited

U.S. PATENT DOCUMENTS

| 2,267,961 A | 12/1941 | Tilyer et al. |
| 5,617,213 A | 4/1997 | Shih |

(Continued)

FOREIGN PATENT DOCUMENTS

| CN | 202024963 U | 11/2011 |
| CN | 203132817 U | 8/2013 |

OTHER PUBLICATIONS

International Search Report mailed May 12, 2013; PCT/CN2013/073901.

(Continued)

*Primary Examiner* — Michael P Stafira
(74) *Attorney, Agent, or Firm* — Ladas & Parry LLP

(57) ABSTRACT

A transmittance testing apparatus includes a frame bearing rod for support, and a light emitter carriage, a DUT carriage and a light receiver carriage supported by the frame bearing rod from bottom up; the light emitter carriage is used for placing a light emitter capable of emitting light, the DUT carriage is used for mounting a touch sensor, a light receiver carriage is used for placing a light receiver facing the DUT carriage. Positions of the light emitter, the touch sensor and the light receiver in the apparatus are fixed with respect to each other Thus, stable and accurate measurement of transmittance can be obtained.

20 Claims, 3 Drawing Sheets

(56) References Cited

U.S. PATENT DOCUMENTS

| | | | |
|---|---|---|---|
| 7,893,706 B2* | 2/2011 | Lee | 324/760.02 |
| 8,890,067 B2* | 11/2014 | Park et al. | 250/310 |
| 2001/0012069 A1* | 8/2001 | Derndinger et al. | 348/295 |
| 2005/0035311 A1* | 2/2005 | Asakawa et al. | 250/559.16 |
| 2005/0254045 A1* | 11/2005 | Weiss et al. | 356/237.5 |
| 2009/0215347 A1* | 8/2009 | Lee | 445/3 |

OTHER PUBLICATIONS

International Preliminary Report on Patentability issued Sep. 1, 2015; PCT/CN2013/073901.

* cited by examiner

Topview position C-C'

Topview position B-B'

Topview position A-A'

TRANSMITTANCE TESTING APPARATUS

TECHNICAL FIELD

Embodiments of the present invention relates to a transmittance testing apparatus.

BACKGROUND

Currently, CA-210 Color Analyzer, commercially available from Konica Minolta Corporation, Japan, is used to manually measure transmittance of a touch sensor in a liquid crystal display (LCD). Generally, the measurement is carried out by means of choosing randomly and testing five points on the touch sensor. However, such manually testing method can not guarantee uniformity of positions and distances between the CA-210 Color Analyzer and the touch sensor, and therefore such testing results are in low accuracy.

SUMMARY

Embodiments of the present application provide a transmittance testing apparatus which can improve the accuracy of testing results for transmittance of a touch sensor.

According to one aspect of the present application, a transmittance testing apparatus is provided, which comprising a frame bearing rod for support, and a light emitter carriage, a device under test (DUT) carriage and a light receiver carriage which are supported by the frame bearing rod from bottom up, wherein the light emitter carriage is configured for placing a light emitter capable of emitting light, the DUT carriage is configured for mounting a touch sensor, and the light receiver carriage is configured for placing a light receiver facing the DUT carriage.

In the apparatus, for example, a DUT height adjusting knob is further provided on the DUT carriage for adjusting a height of the DUT carriage on the frame bearing rod; and/or, a light receiver height adjusting knob is further provided on the light receiver carriage for adjusting a height of the light receiver carriage on the frame bearing rod.

In the apparatus, for example, a scaler is further configured at a position between the DUT carriage and the light emitter carriage on the frame bearing rod.

In the apparatus, for example, a horizontal coordinate adjuster configured for controlling the light receiver to move in a horizontal plane with respect to the touch sensor is provided on the light receiver carriage; and/or a horizontal coordinate adjuster configured for controlling the touch sensor to move in a horizontal plane with respect to the light receiver is provided on the DUT carriage.

In the apparatus, for example, the horizontal coordinate adjusters comprise an x-direction coordinate adjuster and a y-direction coordinate adjuster.

In the apparatus, for example, a scaler is configured covering a movement range of the x-direction coordinate adjuster; and/or, a scaler is configured covering a movement range of the y-direction coordinate adjuster.

In the apparatus, for example, the touch sensor is mounted on the DUT carriage by means of an attaching clamp.

In the apparatus, for example, a sleeve is further configured on the frame bearing rod and the sleeve is connected to a microscope through a microscope-connection bar. The sleeve is capable of rotating around the frame bearing rod and sliding in the up-down direction, and the microscope-connecting bar is a stretchable connecting bar capable of rotating axially.

In the apparatus, for example, a sleeve is configured on the frame bearing rod and the sleeve is connected to a probe by means of a probe-connection bar. The sleeve is capable of rotating around the frame bearing rod and sliding in the up-down direction, and the probe-connection bar is a stretchable connecting bar capable of rotating axially.

In the apparatus, for example, a flexible printed circuit-board (FPC) is further configured on the DUT carriage, and the FPC is connected to the touch sensor for inputting touch signals into the touch sensor.

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

REFERENCE NUMERALS

1, Frame bearing rod; 2, Light receiver Carriage; 3, DUT carriage; 4, Light emitter carriage; 5, Light receiver X-direction adjuster for; 6, Light receiver height adjusting knob; 7, Light receiver; 8, Light transmission tube; 9, Light receiver X-direction coordinate adjuster; 10, DUT height adjusting knob; 11, Attaching clamp; 12, Flexible Printed Circuit Board; 13, LCD display module (LCM); 14, Scaler; 15, Sleeve; 16, Microscope-connection bar; 17, Microscope; 18, Sleeve; 19, Probe-connection bar; 20 Probe; 21, Line Port; 22, Regulator of FPC; 23, Level Meter; 24, Touch Sensor; 25, Scaler

DETAILED DESCRIPTION

In order to make objects, technical details and advantages of the embodiments of the invention apparent, the technical solutions of the embodiment will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

Unless otherwise defined, technical terms or scientific terms used herein should be construed as general meanings that those skilled in the art understand. The terms "a", "an", "the" and the like used before an element are not limitative in term of quantity, and just denote the presence of at least one of such element. The terms "comprising", "including" and the like means that the element or the thing before "comprising" or "including" contains elements or things and the like listed behind "comprising" or "including", and do not exclude other elements or things. The terms "connection", "link" and the like are not limited to a physical or mechanical connection or link, and may also comprise electrical connection, whatever direct or indirect. The terms "on", "below", "left", "right" and the like are only intended to denote relative positional relationship of objects, and the relative positional relationship may change correspondingly if absolute positions of the described objects change.

Figure 1:
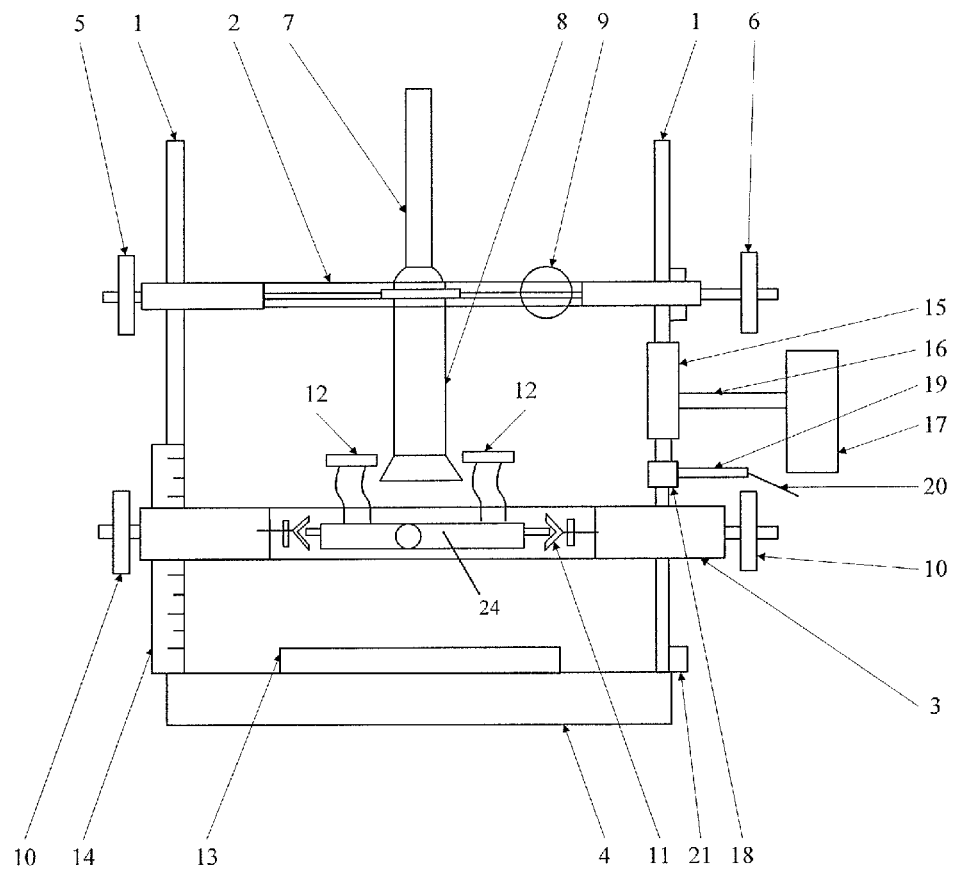
FIG. 1 is a structural diagram of the transmittance testing apparatus according to an embodiment of the present application.

The transmittance testing apparatus according to an embodiment of the present invention can be configured as the structure as illustrated in FIG. 1. A frame bearing rod 1 can mount and support a light emitter carriage 4, a device under test (DUT) carriage 3 and a light receiver carriage 2 from bottom up. For example, the profiles of the light emitter carriage 4, the DUT carriage 3 and the light receiver carriage 2 can be a rectangular or a square, but they are not limited to such cases and can be configured to be of any shape according to actual requirement.

An LCD display module (LCM) or the like capable of emitting light can be placed on the light emitter carriage 4. One or more mounting clamps 11 are configured on the DUT carriage 3 and the mounting clamps 11 can mount a device under test such as a touch sensor 24 horizontally on the DUT carriage 3. A light receiver 7 facing the DUT carriage 3 is configured on the light receiver carriage 2. A light transmission tube 8 which is connected tightly with the light receiver 7 and faces the DUT carriage 3 is configured between the light receiver 7 and the DUT carriage 3. The light receiver 7 and the light transmission tube 8 may be integrated. For example, the light receiver 7 can be a testing apparatus for transmittance such as CA-210 Color Analyzer, or can be an optical fiber for guiding light into a testing apparatus for transmittance such as CA-210 Color Analyzer, and the protection scope of the present invention is not limited thereto.

Assuming a device under test mounted on the DUT carriage 3 is a touch sensor 24, the light emitted from the LCM 13 will be received by the light receiver 7 via the light transmission tube 8 after passing through the touch sensor 24. Then, the transmittance of the touch sensor 24 can be determined according to the quantity of the light received by the light receiver 7 and the quantity of light originally emitted from the LCM 13.

It can be seen that, as the frame bearing rod 1 can fix and bear the light emitter carriage 4, the DUT carriage 3, and the light receiver carriage 2, a distance between the light emitter carriage 4 and the DUT carriage 3 and a distance between the DUT carriage 3 and the light receiver carriage 2 can be set when the apparatus is originally designed, such that a proper light transmission distance between the LCM 13 on the light emitter carriage 14 and the touch sensor 24 on the DUT carriage 3 can be obtained; also, a distance between the touch sensor 24 on the DUT carriage 3 and the light transmission tube 8 on the light receiver carriage 2 is small enough to ensure that the light emitted from the LCM 13 can be received effectively by the light receiver 7 via the light transmission tube 8 after passing through the touch sensor 24. In the example described above, the positions of the LCM 13, the touch sensor 24 and the light receiver 7 are fixed, and are not subjected to easy changes as that in the manual measurement of conventional techniques. Thus, stable and accurate test data can be obtained in such stable testing conditions. Further, stable and accurate measurement of transmittance of the touch sensor 24 can be obtained. The accuracy of the measurement of the transmittance of the touch sensor 24 is highly improved with respect to the conventional techniques.

In one example, a DUT height adjusting knob 10 can be configured on the DUT carriage 3 in order to improve flexibility in the operation of the testing apparatus for transmittance according to the present invention. DUT height adjusting knobs 10 can be configured on both sides of the DUT carriage 3, as illustrated in FIG. 1. The height of the DUT carriage 3 on the frame bearing rod 1 can be adjusted by means of the DUT height adjusting knob(s) 10, such that the distance between the touch sensor 24 mounted on the DUT carriage 3 and the LCM 13 on the light emitter carriage 4 become adjustable. Additionally, a scaler 14 can be configured on the frame bearing rod 1 between the DUT carriage 3 and the light emitter carriage 4, such that the distance between the touch sensor 24 mounted on the DUT carriage 3 and the LCM 13 on the light emitter carriage 4 can be precisely quantized. For example, the scaler 14 can be configured on the left side.

In one example, a light receiver height adjusting knob 6 can be configured on the light receiver carriage 2. For example, the light receiver height adjusting knob 6 is configured on the left side. The height of the light receiver carriage 2 on the frame bearing rod 1 can be adjusted by means of the light receiver height adjusting knob 6, such that a distance between the light transmission tube 8 on the light receiver carriage 2 and the touch sensor 24 mounted on the DUT carriage 3 become adjustable.

To make the test results of the transmittance more accurate, a multiple points test can be performed for the touch sensor 24. To this end, a horizontal coordinate adjuster can be configured on the light receiver carriage 2, such that the light receiver 7 can move in a horizontal plane with respect to the touch sensor 24 which is mounted with the mounting clamps 11. The horizontal coordinate adjuster can be implemented in various manners, such as a slide rail, a lead screw and the like mechanical structures, as long as the coordinate of the light receiver 7 in the horizontal plane can be adjusted. In this way, the light receiver 7 can move in a horizontal plane over the touch sensor 24 mounted on the DUT carriage 3, and can receive light passing through different positions of the touch sensor, so that a multiple-point test is achieved for the touch sensor 24.

For example, the horizontal coordinate adjuster may comprise a light receiver x-direction coordinate adjuster 5 and a light receiver y-direction coordinate adjuster 9; the light receiver x-direction coordinate adjuster 5 can adjust the coordinate of the light receiver 7 on the x-axis, and the light receiver y-direction coordinate adjuster 9 can adjust the coordinate of the light receiver 7 on the y-axis. In one example, a scaler 25 can be configured on the light receiver 2 so as to quantize the movement position of the horizontal coordinate adjuster. For example, a scaler 25 covering the movement range of the light receiver x-direction coordinate adjuster 5 is configured on the light receiver carriage 2 so as to quantize the movement position of the light receiver x-direction coordinate adjuster 5; and/or, a scaler 25 covering the movement range of the light receiver 9-direction coordinate adjuster 9 is configured on the light receiver carriage 2 so as to quantize the movement position of the light receiver y-direction coordinate adjuster 9.

It should be noted that, a horizontal coordinate adjuster may not be configured on the light receiver carriage 2 while based on the same principle a horizontal coordinate adjuster is configured on the DUT carriage 3 and is used for adjusting the coordinates of the mounting clamps 11 in the horizontal plane so that the touch sensor 24 mounted with the mounting clamps 11 can move in the horizontal plane with respect to the light receiver 7. The horizontal coordinate adjuster can be implemented in various manners, such as a slide rail, a lead screw or the like mechanical structures, as long as the coordinates of the light receiver 24 in the horizontal plane can be adjusted. Of course, horizontal coordinate adjusters can be configured on both the light carriage 2 and the DUT carriage 3.

In order to achieve multifunction of the transmittance testing apparatus according to the present invention, in one example, a sleeve 15 can be configured on the frame bearing rod 1 and the sleeve 15 is connected to a microscope 17 by means of a microscope-connection bar 16. The sleeve 15 can sleeve the frame bearing rod 1, and can rotate around it and slide up-down along it, and the microscope-connection bar 16 may be a stretchable bar which can rotate axially. In this way, the microscope 17 can move to over the touch sensor 24 mounted on the DUT carriage 3 by means of the rotation and the up-down sliding movement of the sleeve 15, and even the microscope 17 can be fine-adjusted though the rotation and the stretch of the microscope-connection bar 16, such that an operator can observe the touch sensor 24 by means of the microscope 17 in order to inspect defects of the touch sensor 24.

Moreover, a sleeve 18 can be configured on the frame bearing rod 1 and the sleeve 18 is connected to a prove 20 by means of a probe-connection bar 19. The sleeve 18 can sleeve the frame bearing rod 1, and can rotate around it and slide up-down along it, and the probe-connection bar 19 may be a stretchable bar which can rotate axially. In this way, the probe 20 can move to over the touch sensor 24 mounted on the DUT carriage 3 by means of the rotation and the up-down sliding of the sleeve 18, and even it can be fine-adjusted by means of the rotation and stretch of the probe-connection bar 19 such that an operator can probe the positions of the pins of the touch sensor 24 by means of the probe 20.

Furthermore, in one example, an FPC 12 connecting to the touch sensor 24 is configured on the DUT carriage 3, and the FPC 12 can input touch signals into the touch sensor 24. Then, bonding signal interference is liable to occur between the touch sensor inputted touch signals and the LCM 13 placed on the light emitter carriage 4, and an operator can detect the bonding signal interference by instruments such as the microscope 17, the probe 20 or the like. In order to support the input of the touch signals and other signal processing devices that may be needed, a line port 21 for wiring is configured on the frame bearing rod 1 so as to enable transmission of signals. In one example, an FPC regulator also can be configured on the frame bearing rod 1 or the like in order to control specific parameters such as signal quantity and applications of the FPC 12.

In one example, a level meter 23 can be placed on at least one of the light emitter carriage 4, the DUT carriage 3 and the light receiver carriage 2.

Figure 2:
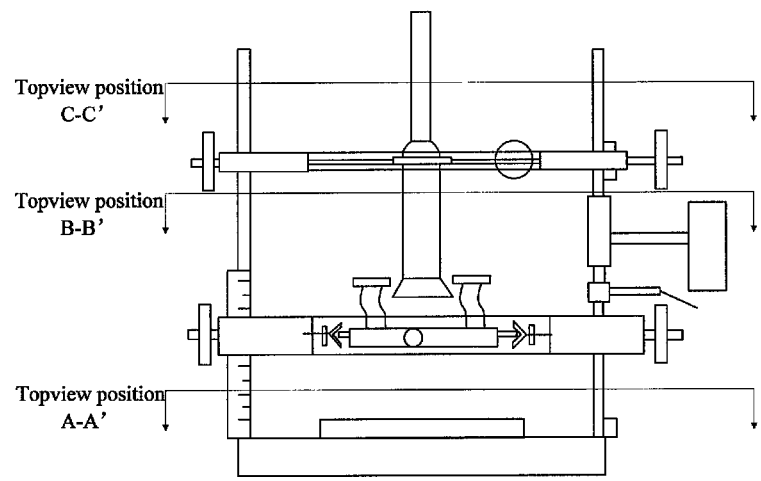
FIG. 2 is a structural schematic diagram of the transmittance testing apparatus according to an embodiment of the present application viewed top-down.
Figure 3A:
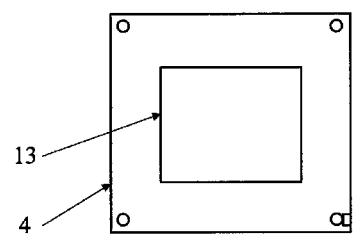
FIGS. 3a to 3c are top views corresponding to the different tor-viewing positions A-A', B-B' and C-C' in FIG. 2, respectively.
Figure 3B:
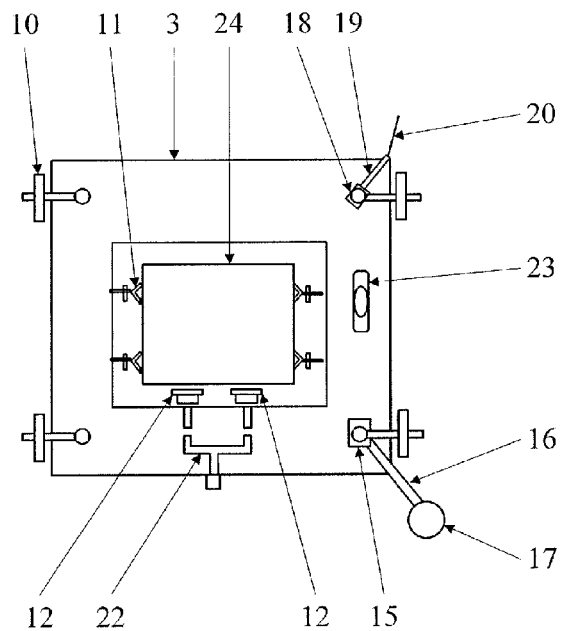
Figure 3C:
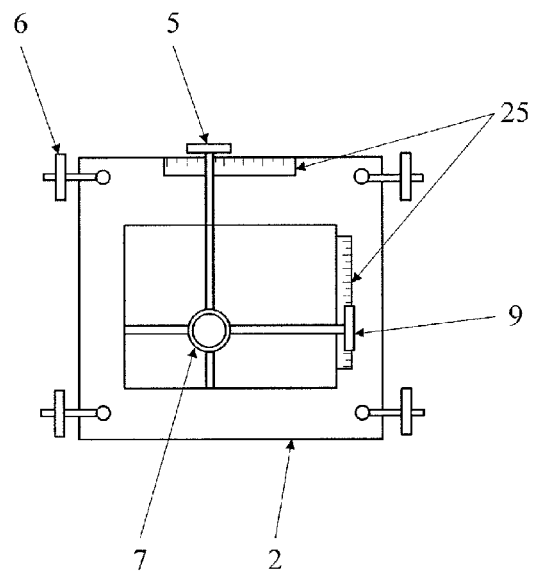

In order to make the foregoing description more clear, corresponding top views are provided according to various topview positions of the transmittance testing apparatus as illustrated in FIG. 2. FIG. 3a is the top view at the position A-A' in FIG. 2 (relating to the light emitter carriage 4), FIG. 3b is the top view at the position B-B' in FIG. 2 (relating to the DUT carriage 3), and FIG. 3c is the top view at the position C-C' in FIG. 2 (relating to the light receiver carriage 2). The devices in the FIGS. 3a to 3c have been described in the foregoing description, and will be not repeated here.

It can be understood from the foregoing description that, in the transmittance testing apparatus according to the embodiment of the present application, the positions of the light emitter, the touch sensor and the light receiver are fixed with respect to each other, and can not be easily changed as those in the manual measurement of conventional techniques. Thus, stable and accurate measurement can be obtained under such stable testing conditions, and furthermore stable and accurate measurement of transmittance of the touch sensor can be achieved. So, the accuracy of the measurement for the transmittance of the touch sensor is obviously improved compared with the conventional techniques. Furthermore, the transmittance testing apparatus according to the present invention can have other functions such as detecting defects of the touch sensor, and diversification of testing can be achieved.

The foregoing are merely exemplary embodiments of the invention, but are not used to limit the protection scope of the invention. The protection scope of the invention shall be defined by the attached claims.

The invention claimed is:

1. A transmittance testing apparatus comprising a frame bearing rod for support, and a light emitter carriage, a device under test (DUT) carriage and a light receiver carriage which are supported by the frame bearing rod from bottom up;
   wherein the light emitter carriage is configured for placing a light emitter capable of emitting light, the DUT carriage is configured for mounting a touch sensor; and the light receiver carriage is configured for placing a light receiver facing the DUT carriage, and
   a DUT height adjusting knob configured for adjusting a height of the DUT carriage on the frame bearing rod with respect to the light emitter carriage is provided on the DUT carriage.

2. The apparatus according to the claim 1, wherein a light receiver height adjusting knob configured for adjusting a height of the light receiver carriage on the frame bearing rod is provided on the light receiver carriage.

3. The apparatus according to claim 1, wherein a scaler is configured at a position between the DUT carriage and the light emitter carriage on the frame bearing rod.

4. The apparatus according to claim 1, wherein
   a horizontal coordinate adjuster configured for controlling the light receiver to move in a horizontal plane with respect to the touch sensor is provided on the light receiver carriage; and/or
   a horizontal coordinate adjuster configured for controlling the touch sensor to move in a horizontal plane with respect to the light receiver is provided on the DUT carriage.

5. The apparatus according to claim 4, wherein the horizontal coordinate adjuster comprises an x-direction coordinate adjuster and a y-direction coordinate adjuster.

6. The apparatus according to claim 5, further comprising a scaler covering a movement range of the x-direction coordinate adjuster; and/or a scaler covering a movement range of the y-direction coordinate adjuster.

7. The apparatus according to claim 1, wherein the touch sensor is mounted on the DUT carriage by means of a mounting clamp.

8. The apparatus according to claim 1, wherein a sleeve is configured on the frame bearing rod and the sleeve is connected to a microscope through a microscope-connection bar;
   the sleeve is capable of rotating around and sliding up-down on the frame bearing rod, and the microscope-connection bar is a stretchable connecting bar capable of rotating axially.

9. The apparatus according to claim 1, wherein a sleeve is configured on the frame bearing rod and is connected to a probe by means of a probe-connection bar;
   the sleeve is capable of rotating around and sliding up-down on the frame bearing rod, and the probe-connection bar is a stretchable connecting bar capable of rotating axially.

10. The apparatus according to claim 1, wherein an flexible printed circuit-board (FPC) is configured on the DUT carriage and is connected to the touch sensor for inputting touch signals into the touch sensor.

11. The apparatus according to claim 2, wherein
a horizontal coordinate adjuster configured for controlling the light receiver to move in a horizontal plane with respect to the touch sensor is provided on the light receiver carriage; and/or
a horizontal coordinate adjuster configured for on oiling the touch sensor to move in a horizontal plane with respect to the light receiver is provided on the DUT carriage.

12. The apparatus according to claim 11, wherein the horizontal coordinate adjuster comprises an x-direction coordinate adjuster and a y-direction coordinate adjuster.

13. The apparatus according to claim 12, further comprising a scaler covering a movement range of the x-direction coordinate adjuster; and/or a scaler covering a movement range of the y-direction coordinate adjuster.

14. The apparatus according to claim 3, wherein
a horizontal coordinate adjuster configured for controlling the light receiver to move in a horizontal plane with respect to the touch sensor is provided on the light receiver carriage; and/or
a horizontal coordinate adjuster configured for controlling the touch sensor to move in a horizontal plane with respect to the light receiver is provided on the DUT carriage.

15. The apparatus according to claim 14, wherein the horizontal coordinate adjuster comprises an x-direction coordinate adjuster and a y-direction coordinate adjuster.

16. The apparatus according to claim 15, further comprising a scaler covering a movement range of the x-direction coordinate adjuster; and/or a scaler covering a movement range of the y-direction coordinate adjuster.

17. The apparatus according to claim 4, wherein the touch sensor is mounted on the DUT carriage by means of a mounting clamp.

18. The apparatus according to claim 4, wherein a sleeve is configured on the frame bearing rod and the sleeve is connected to a microscope through a microscope-connection bar;
the sleeve is capable of rotating around and sliding up-down on the frame bearing rod, and the microscope-connection bar is a stretchable connecting bar capable of rotating axially.

19. The apparatus according to claim 4, wherein a sleeve is configured on the frame bearing rod and is connected to a probe by means of a probe-connection bar;
the sleeve is capable of rotating around and sliding up-down on the frame bearing rod, and the probe-connection bar is a stretchable connecting bar capable of rotating axially.

20. The apparatus according to claim 4, wherein an flexible printed circuit-board (FPC) is configured on the DUT carriage and is connected to the touch sensor for inputting touch signals into the touch sensor.

* * * * *

UNITED STATES PATENT AND TRADEMARK OFFICE
CERTIFICATE OF CORRECTION

PATENT NO. : 9,182,346 B2  
APPLICATION NO. : 14/236216  
DATED : November 10, 2015  
INVENTOR(S) : Shengji Yang Page 1 of 1

It is certified that error appears in the above-identified patent and that said Letters Patent is hereby corrected as shown below:

Claims

In claim 11, line 6 (column 7, line 6), delete "on oiling" and insert --controlling--.

Signed and Sealed this  
Third Day of May, 2016

Michelle K. Lee  
*Director of the United States Patent and Trademark Office*